(12) United States Patent
De Boni et al.

(10) Patent No.: US 7,364,596 B2
(45) Date of Patent: Apr. 29, 2008

(54) DYE COMPOSITIONS COMPRISING AT LEAST ONE HYDROPHOBIC DIRECT DYE AND AT LEAST ONE ACID

(75) Inventors: Maxime De Boni, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 279 days.

(21) Appl. No.: 11/204,149

(22) Filed: Aug. 16, 2005

(65) Prior Publication Data
US 2006/0031998 A1 Feb. 16, 2006

(30) Foreign Application Priority Data
Aug. 16, 2004 (FR) .................................. 04 51855

(51) Int. Cl.
*A61K 7/13* (2006.01)
(52) U.S. Cl. ..................... 8/405; 8/406; 8/407; 8/410; 8/411; 8/421; 8/425; 8/428; 8/455; 8/456
(58) Field of Classification Search ................... 8/405, 8/406, 407, 410, 411, 421, 425, 428, 435, 8/455, 456
See application file for complete search history.

(56) References Cited

U.S. PATENT DOCUMENTS

| | | | |
|---|---|---|---|
| 3,816,529 A * | 6/1974 | Loffelman | .................. 564/163 |
| 5,593,459 A | 1/1997 | Gamblin | |
| 5,708,151 A | 1/1998 | Möckli | |
| 5,891,200 A | 4/1999 | Lim et al. | |
| 6,172,242 B1 | 1/2001 | Eyal et al. | |
| 6,206,935 B1 * | 3/2001 | Onitsuka et al. | ................ 8/431 |
| 6,231,622 B1 | 5/2001 | Chassot et al. | |
| 6,432,147 B1 | 8/2002 | Dias et al. | |
| 2002/0032933 A1 | 3/2002 | Dias et al. | |
| 2004/0045101 A1 | 3/2004 | Miczewski et al. | |

FOREIGN PATENT DOCUMENTS

| | | |
|---|---|---|
| DE | 41 22 748 A1 | 1/1993 |
| EP | 0714 954 B1 | 6/1996 |
| EP | 1 153 599 A2 | 11/2001 |
| EP | 1 366 752 A1 | 12/2003 |
| EP | 1 369 105 A1 | 12/2003 |
| JP | 2000-143466 | 5/2000 |
| JP | 2000-514829 | 11/2000 |
| JP | 2003-246715 | 9/2003 |
| WO | WO 95/01772 | 1/1995 |
| WO | WO 95/15144 | 6/1995 |
| WO | WO 98/27945 | 7/1998 |

OTHER PUBLICATIONS

STIC Search Report dated on Jun. 8, 2007.*
French Search Report for FR 04 51855, dated Mar. 16, 2005.
Kirshna L. Bhat et al., "Calculated Values of the Octanol-Water Partition Coefficient and Aqueous Solubility for Aminoazobenzene Dyes and Related Structures," Dyes and Pigments, vol. 52, pp. 145-159, 2002.
William M. Meylan et al., "Atom/Fragment Contribution Method for Estimating Octanol-Water Partition Coefficient", Journal of Pharmaceutical Sciences, vol. 84, No. 1, 1995, pp. 83-92.
English language Derwent Abstract of DE 41 22 748 A1, Jan. 14, 1993.
English language abstract of JP 2003-246715, Sep. 2, 2003.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure provides dye compositions comprising at least one hydrophobic direct dye with a logP of greater than 2, at least one organic or mineral acid with a pKa of less than 4.5, in an aqueous-alcoholic dyeing medium comprising at least 60% by weight of water relative to the total weight of the composition, the pH of the composition being less than 7.

The compositions allow shades ranging from pastel to strong colorations to be obtained on keratin fibers. Furthermore, the coloration obtained makes it possible to achieve or even exceed the fastness of oxidation dyeing.

31 Claims, No Drawings

DYE COMPOSITIONS COMPRISING AT LEAST ONE HYDROPHOBIC DIRECT DYE AND AT LEAST ONE ACID

This application claims benefit of priority under 35 U.S.C. § 119 to French patent application No. 04/51855, filed Aug. 16, 2004, the contents of which are hereby incorporated by reference.

The present disclosure relates to dye compositions comprising, in suitable media, particular hydrophobic dyes and acids. The present disclosure also relates to uses of these compositions for dyeing keratin fibers and dyeing processes using these compositions.

For a long time, people have tried to modify the color of their hair, for example, to mask their grey hair.

To do this, it is known practice to permanently dye keratin fibers by oxidation dyeing. This dyeing technique comprises applying to the keratin fibers a composition containing dye precursors such as oxidation bases and couplers. These precursors, under the action of an oxidizing agent, form one or more colored species in the hair.

The variety of molecules used as oxidation bases and couplers allows for a rich palette of colors to be obtained. The resulting colorations may be permanent, strong and/or resistant to external agents, such as light, bad weather, washing, perspiration, and rubbing.

However, this type of coloration is performed using oxidizing products such as aqueous hydrogen peroxide solutions in basic media. Such oxidizing agents may attack the keratin of the hair, with the result that the cosmetic and mechanical properties of the keratin may become substantially degraded, for example, in the case of repeated coloration, which may result in difficulty in styling or shaping.

Moreover, it is known practice to dye keratin fibers, including human hair, with dye compositions containing direct dyes. Direct dyes are colored and coloring molecules with an affinity for keratin fibers. Standard dyes that are used include nitrobenzene, anthraquinone, nitropyridine, azo, xanthene, acridine, azine, and triarylmethane dyes as well as natural dyes. These dyes may be nonionic, anionic, cationic or amphoteric.

Direct dyes are generally used in a medium consisting predominantly of water, optionally with a minor amount of solvent such as alcohols. Such compositions are described, for example, in EP 1 366 752 and EP 1 369 105. It is also known practice, in order to improve the solubility in water of dispersed cationic dyes or solvents by addition of an anionic surfactant, described in U.S. Pat. No. 5,593,459.

Compositions such as those above-described containing one or more direct dyes are applied to keratin fibers for a time that is necessary to obtain the desired coloration, and are then rinsed out. The colorations resulting therefrom are colorations that are often chromatic, but that are temporary or semi-permanent. Such direct dyes may have low dyeing power, poor wash-fastness and/or poor perspiration-fastness, due to the nature of the interactions that bind the direct dyes to the keratin fibers, and their desorption from the surface and/or the core of the fiber.

Thus it would be desirable to develop novel direct dye compositions to obtain varied shades, such as pastel shades, which demonstrate good fastness, for example with respect to external agents such as light, shampoo, and sweat. It would also be desirable to develop dye compositions for obtaining colorations that show fastness close to that of oxidation dyeing, without the drawbacks associated with the presence of an oxidizing agent.

The present disclosure provides dye compositions comprising at least one hydrophobic direct dye with a logP of greater than 2 and at least one organic or mineral acid with a pKa of less than 4.5, in an aqueous-alcoholic dyeing medium comprising at least 60% by weight of water relative to the total weight of the composition, wherein the composition has a pH of less than 7.

The presently disclosed compositions allow shades ranging from pastel to strong colorations to be obtained. Furthermore, the colorations obtained may make it possible to achieve or even exceed the fastness of oxidation dyeing. Thus, the colorations obtained may be highly resistant to external agents, such as repeated washing.

As used herein, the logP value conventionally represents the partition coefficient of the dye between octanol and water. The logP value may be calculated according to the method described in Meylan & Howard, *Atom/Fragment contribution method for estimating octanol-water partition coefficient*, J. Pharm. Sci., 84, 83-92 (1995). This value may also be calculated using a range of commercially available software that determines the logP value as a function of the structure of a molecule, for example, Epiwin software from the United States Environmental Protection Agency.

Direct dyes that may be used include hydrophobic dyes known in the art, which have a logP value of greater than 2. Examples include:

| Dye | Chemical structure | LogP |
|---|---|---|
| Disperse Red 13 | (structure shown) | 5.22 |
| Disperse Green 9 | (structure shown) | 4.23 |

-continued

| Dye | Chemical structure | LogP |
| --- | --- | --- |
| Solvent Black 3 | 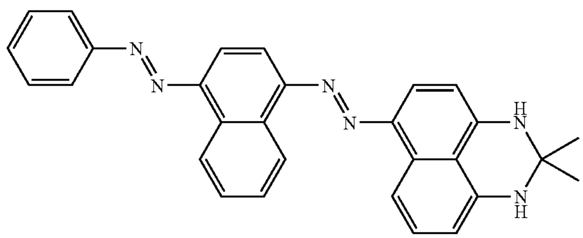 | 7.50 |
| Disperse Blue 148 | 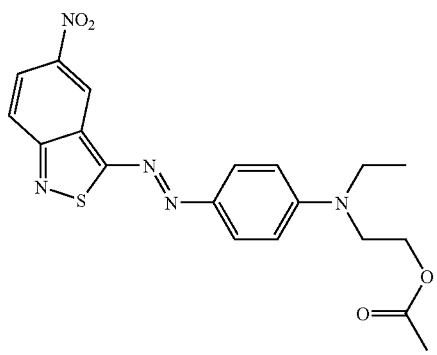 | 4.81 |
| Disperse Violet 63 | 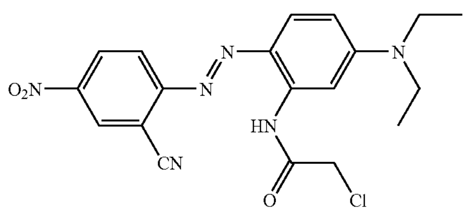 | 5.30 |
| Disperse Blue 60 | 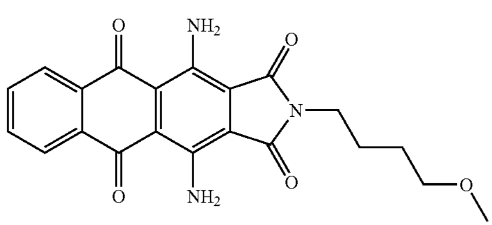 | 3.38 |
| Disperse Blue 14 | 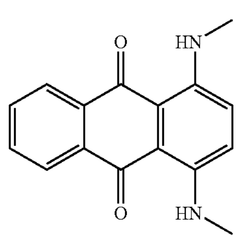 | 4.25 |
| Solvent Orange 15 | 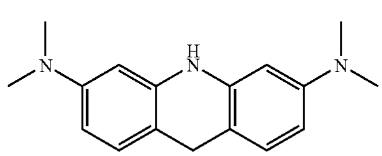 | 3.90 |

-continued

| Dye | Chemical structure | LogP |
|---|---|---|
| Solvent Orange 7 | 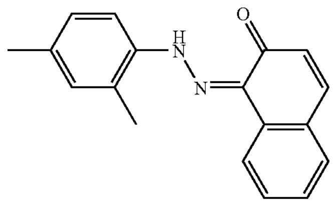 | 4.40 |
| Solvent Blue 14 | 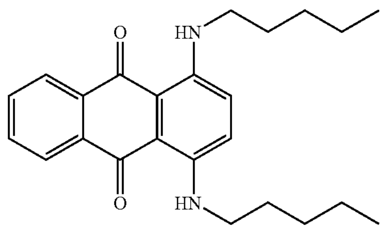 | 8.18 |
| Disperse Yellow 82 | 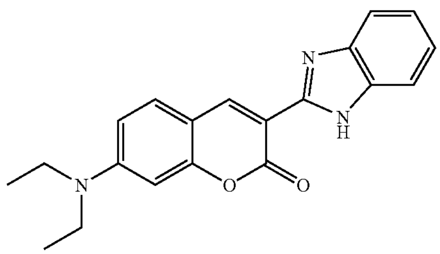 | 3.68 |

In some embodiments, the logP of the dyes useful in the presently claimed compositions is greater than 4.

The direct dye or dyes with a logP of greater than 2 may be present in the composition in amounts ranging from 0.001% to 5% by weight relative to the total weight of the composition.

The organic acid with a pKa of less than 4.5 may be chosen, for example, from benzoic acid, salicylic acid, benzenesulfonic acid and mixtures thereof, for example, benzoic acid.

The mineral acid with a pKa of less than 4.5 may be chosen, for example, from phosphoric acid, hydrochloric acid, and sulfuric acid.

The compositions disclosed herein may comprise mixtures of one or more organic or mineral acids. In some embodiments, the acid is an organic acid.

In some embodiments, the compositions disclosed herein may further comprise a divalent mineral acid salt. Divalent mineral acids include, for example, ammonium sulfate, sodium hydrogen phosphate, sodium carbonate and mixtures thereof, for example, ammonium sulfate.

The amount of organic acid, of mineral acid and of divalent mineral acid salts may range from 0.001% to 10%, such as from 0.05% to 2%, by weight relative to the total weight of the composition.

In some embodiments, the amount of water in the aqueous-alcoholic dyeing medium ranges from 60% to 99.5% by weight, for example, from 60% to 90% or even 70% to 85%, by weight relative to the total weight of the composition.

The dyeing media of the presently disclosed compositions are aqueous-alcoholic mixtures. Alcohols that may be used include, but are not limited to, $C_1$-$C_6$ lower alkanols, and polyols and polyol ethers comprising a free —OH function. Examples include 2-butoxyethanol, propylene glycol, propylene glycol monomethyl ether, diethylene glycol monomethyl ether, diethylene glycol monoethyl ether, ethylene glycol monoethyl ether, ethylene glycol monobutyl ether, neopentyl glycol, and isoprene glycol. Aromatic alcohols may also be used, for example, benzyl alcohol, phenoxyethanol, phenylethyl alcohol, ethanol, isopropanol, n-propanol, butanol, n-pentanol, 1,2-propanediol, 1,3-propanediol, 1-methoxy-2-propanol, 1-ethoxy-2-propanediol, 1,3-butanediol, 1,4-butanediol, and 1,2-hexanediol. Mixtures of these alcohols may also be used.

In some embodiments, the amount of alcohol is greater than or equal to 5%, for example, from 5% to 35% or from 10% to 25%. The percentages are weight percentages relative to the total weight of the compositions.

The presently disclosed dye compositions may further comprise direct dyes other than the at least one hydrophobic direct dye. These additional direct dyes may be chosen from, for. example, neutral, acidic or cationic nitrobenzene direct dyes, neutral, acidic or cationic azo direct dyes, neutral, acidic or cationic quinone (such as anthraquinone) direct dyes, azine direct dyes, triarylmethane direct dyes, indoamine direct dyes, and natural direct dyes.

Benzene-based direct dyes useful herein include, but are not limited to, the following compounds:
1,4-diamino-2-nitrobenzene,
1-amino-2-nitro-4-(β-hydroxyethylamino)benzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene, 1-β-hydroxyethylamino-2-nitro-4-(ethyl)(β-hydroxyethyl) aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-[tris(hydroxymethyl)methylamino]-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-[bis(β-hydroxyethyl)amino]-3-nitrobenzene,
1-β-hydroxyethylamino-2-nitrobenzene, and
1-hydroxy-4-β-hydroxyethylamino-3-nitrobenzene.

Azo direct dyes useful herein, include, but are not limited to, the cationic azo dyes described in patent applications WO95/15144, WO95/01772, and EP714 954, each hereby incorporated by reference.

These cationic azo dyes include but are not limited to:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Azo direct dyes that may also be used include, but are not limited to, the following dyes described in the Color Index International 3rd Edition:
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23, and
Acid Orange 24.

1-(4'-Aminodiphenylazo)-2-methyl-4-[bis(β-hydroxyethyl)amino]benzene, and 4-hydroxy-3-(2-methoxyphenylazo)-1-naphthalenesulfonic acid may also be used.

Quinone direct dyes useful herein, include, but are not limited to, the following dyes:
Acid Violet 43,
Acid Blue 62,
Basic Blue 22,
Basic Blue 99,
and also the following compounds:
1-N-methylmorpholiniumpropylamino-4-hydroxyanthraquinine,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Azine dyes useful herein include but are not limited to:
Basic Blue 17, and
Basic Red 2.

Triarylmethane dyes useful herein, include but are not limited to, the following compounds:
Basic Green 1,
Acid Blue 9,
Basic Violet 3,
Basic Violet 14,
Basic Blue 7,
Acid Violet 49,
Basic Blue 26, and
Acid Blue 7.

Natural direct dyes useful herein include but are not limited to lawsone, juglone, alizarin, purpurin; carminic acid, kermesic acid, and spinulosin. Extracts and decoctions comprising these natural dyes may also be used, for example, henna-based poultices or extracts.

In embodiments when the presently disclosed compositions comprise direct dyes other than those with a logP of greater than or equal to 2, the compositions may comprise up to 20% of direct dyes. According to these embodiments, the compositions may comprise a total amount of direct dyes ranging from 0.001% to 10% by weight.

The presently disclosed compositions may further comprise oxidation bases and couplers conventionally used in oxidation dyeing.

Oxidation bases that may be used include but are not limited to para-phenylenediamines, bis(phenyl)alkylenediamines, para-aminophenols, ortho-aminophenols, heterocyclic bases, and addition salts thereof.

Couplers that may be used include but are not limited to meta-phenylene-diamine couplers, meta-aminophenol couplers, meta-diphenol couplers, naphthalene-based couplers, heterocyclic couplers, and addition salts thereof.

When present, the oxidation bases and couplers may each be present in an amount ranging from 0.001% to 10%, such as from 0.005% to 6%, by weight relative to the total weight of the dye composition.

The dye compositions disclosed herein may also comprise one or more of various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, such as anionic, cationic, nonionic and amphoteric polymeric associative thickeners, antioxidants, penetrating agents, sequestering agents, fragrances, buffers, dispersants, conditioners, for example, volatile or non-volatile, modified or unmodified silicones, film-forming agents, ceramides, preserving agents, and opacifiers.

The adjuvants may each be present in an amount ranging from 0.01% to 20% by weight relative to the weight of the composition.

A person skilled in the art will take care to select optional additional compound(s) such that the properties intrinsically associated with the presently disclosed dye compositions are not, or are not substantially, adversely affected by the envisaged addition(s).

The pH of the presently disclosed dye compositions, which is less than 7, may be adjusted to the desired value by means of acidifying or basifying agents used for dyeing keratin fibers and/or by means of standard buffer systems.

Acidifying agents useful herein include, but are not limited to, mineral and organic acids, for instance hydrochloric acid, orthophosphoric acid, sulfuric acid, carboxylic acids, for example, acetic acid, tartaric acid, citric acid, lactic acid, and sulfonic acids.

Basifying agents useful herein include, but are not limited to, aqueous ammonia, alkaline carbonates alkanolamines such as monoethanolamine, diethanolamine, triethanolamine, and derivatives thereof, sodium hydroxide, potassium hydroxide, and the compounds of formula (III) below:

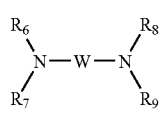

(III)

wherein W is a propylene residue optionally substituted with a radical chosen from hydroxyl and a $C_1$-$C_4$ alkyl radical; and $R_6$, $R_7$, $R_8$ and $R_9$, which may be identical or different, are chosen from a hydrogen atom, a $C_1$-$C_4$ alkyl radical, and a $C_1$-$C_4$ hydroxyalkyl radical.

For the dyeing of human keratin fibers, the dyeing medium is a cosmetic medium.

The present disclosure also provides direct dyeing processes comprising applying to keratin fibers a dye composition as defined above for a time sufficient to obtain a desired coloration. The leave-in time generally ranges from 1 to 60 minutes, for example, from 10 to 60 minutes. After the leave-in time, the keratin fibers are rinsed, to reveal dyed fibers.

In some embodiments, the temperature of the composition during the application is less than or equal to 60° C., for example, ranging from room temperature (25° C.) to 40° C.

When the dye composition comprises an oxidation base and/or a coupler, or when it is desired to perform lightening direct dyeing, the dye composition may further comprise at least one oxidizing agent. The oxidizing agents conventionally used for the oxidation dyeing of keratin fibers include, but are not limited to, hydrogen peroxide; urea peroxide; alkali metal bromates; persalts such as perborates and persulfates; peracids; oxidase enzymes such as peroxidases; 2-electron oxidoreductases such as uricases; and 4-electron oxygenases, for example laccases. In some embodiments, hydrogen peroxide is used.

The at least one oxidizing agent, when used, may be added to the dyeing composition at the time of use, or may be used starting with an oxidizing composition comprising it, which is applied simultaneously with or sequentially to the dyeing composition. The oxidizing composition may also further comprise various adjuvants conventionally used in hair dye compositions and as defined above.

The pH of the oxidizing composition comprising the oxidizing agent is such that, after mixing with the dye composition, the pH of the resulting composition applied to the keratin fibers ranges from 3 to 12, such as from 5 to 11. In some embodiments, the pH is less than 7. The pH may be adjusted to the desired value by means of acidifying or basifying agents usually used in the dyeing of keratin fibers and as defined above.

The composition that is finally applied to the keratin fibers may be in various forms, such as in the form of liquids, creams, gels, or in any other form that is suitable for dyeing keratin fibers, such as human hair.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

The invention is illustrated in greater detail by the examples described below

EXAMPLES

Example 1

A dye composition was made as follows:

| | |
|---|---|
| Ethanol | 15% |
| Benzyl alcohol | 5% |
| Benzoic acid | 5% |
| Disperse Red 13 | 0.3% |
| Water | qs 100 |

The composition was applied to a lock of natural grey hair containing 90% white hairs.

After application for 30 minutes at 35° C., the lock was rinsed and dried. The lock was dyed red.

Example 2

A dye composition was made as follows:

| | |
|---|---|
| Ethanol | 15% |
| Benzyl alcohol | 5% |
| Benzoic acid | 0.2% |
| Disperse Red 13 | 0.3% |
| Water | qs 100 |

The composition was applied to a lock of natural grey hair containing 90% white hairs, a lock of permanent-waved grey hair containing 90% white hairs, and a lock of bleached chestnut-brown hair.

After application for 30 minutes at 40° C., the locks were rinsed and dried. The locks were dyed red.

The dyed locks were then shampooed 10 times according to a cycle comprising the washing of the locks with water, washing with shampoo, rinsing with water and then drying.

The color of the locks before coloration, after coloration and after 10 washes was evaluated in the L*a*b* system using a Minolta® CM 2002 spectrophotometer (Illuminant D65). In this L*a*b* system, L* denotes the intensity, a* denotes the green/red color axis and b* denotes the blue/yellow color axis. The lower the value of L, the darker (stronger) the color.

The coloration rise (ΔE) was calculated according to the following equation:

$$\Delta E = \sqrt{(L^*-L_0^*)^2+(a^*-a_0^*)^2+(b^*-b_0^*)^2}$$

In this equation, L*, a* and b* represent the values measured after dyeing and $L_0^*$, $a_0^*$ and $b_0^*$ represent the values measured before dyeing.

The variation in color before and after 10 shampoos (ΔEc) was calculated by according to the following equation:

$$\Delta Ec = \sqrt{(L_1^*-L^*)^2+(a_1^*-a^*)^2+(b_1^*-b^*)^2}$$

In this equation, L*, a* and b* represent the values measured after dyeing and $L_1^*$, $a_1^*$ and $b_1^*$ represent the values measured after 10 shampoos.

The percentage degradation of the color by washing was calculated by (ΔEc/ΔE)*100.

The results are given in Table 1 below.

Example 4 (Comparative)

Dyeing of the three types of lock described in Example 3 was performed using the following dye composition:

| | |
|---|---|
| Hydroxyethylcellulose (MW 720,000) | 0.72% |
| Decylglucoside | 5% |
| Benzyl alcohol | 4% |
| Polyethylene glycol | 4% |
| Basic Red 51 | 0.2% |
| Water | qs 100 |

After a leave-in time of 30 minutes at room temperature, the locks obtained were dyed red.

The measurement of the percentage degradation was performed under the conditions described in Example 3.

The results are given in Table 1 below.

TABLE 1

| % Color degradation | Example 3 | Example 4 |
|---|---|---|
| Natural grey hair | 27% | 42% |
| Permanent-waved grey hair | 7% | 65% |
| Bleached hair | 7% | 85% |

These results show that the compositions described herein are more wash-fast than those obtained by conventional direct dyeing.

What is claimed is:

1. A dye composition comprising
at least one hydrophobic direct dye having a logP greater than 2 and
at least one organic or mineral acid with a pKa of less than 4.5,
in an aqueous-alcoholic dyeing medium comprising at least 60% water,
wherein the pH of the composition is less than 7.

2. The composition according to claim 1, wherein the at least one hydrophobic direct dye has a logP greater than 4.

3. The composition according to claim 1, wherein the alcohol in the aqueous-alcoholic dyeing medium is chosen from $C_1$-$C_6$ lower alkanols, polyols, polyol ethers, and mixtures thereof.

4. The composition according to claim 3, wherein the alcohol is chosen from 2-butoxyethanol, propylene glycol, propylene glycol monomethyl ether, diethylene glycol monomethyl ether, diethylene glycol monoethyl ether, ethylene glycol monobutyl ether, ethylene glycol monoethyl ether, neopentyl glycol, isoprene glycol, ethanol, isopropanol, n-propanol, butanol, n-pentanol, 1,2-propanediol, 1,3-propanediol, 1-methoxy-2-propanol, 1-ethoxy-2-propanediol, 1,3-butanediol, 1,4-butanediol, 1,2-hexanediol, benzyl alcohol, phenoxyethanol, phenylethyl alcohol, and mixtures thereof.

5. The composition according to claim 1, wherein the amount of water in the aqueous-alcoholic medium ranges from 60% to 99.5% by weight relative to the total weight of the composition.

6. The composition according to claim 5, wherein the amount of water ranges from 60% to 90% by weight relative to the total weight of the composition.

7. The composition according to claim 6, wherein the amount of water ranges from 70% to 85% by weight relative to the total weight of the composition.

8. The composition according to claim 1, wherein the amount of alcohol in the aqueous-alcoholic dyeing medium is greater than or equal to 5% by weight relative to the total weight of the composition.

9. The composition according to claim 8, wherein the amount of alcohol ranges from 5% to 35% by weight relative to the total weight of the composition.

10. The composition according to claim 9, wherein the amount of alcohol ranges from 10% to 25%.

11. The composition according to claim 1, wherein the at least one hydrophobic direct dye is present in an amount ranging from 0.001% to 5% by weight relative to the total weight of the composition.

12. The composition according to claim 1, wherein the at least one organic acid is chosen from benzoic acid, salicylic acid, benzenesulfonic acid and mixtures thereof.

13. The composition according to claim 1, wherein the at least one mineral acid is chosen from phosphoric acid, hydrochloric acid, and sulfuric acid.

14. The composition according to claim 12, wherein the amount of organic acid ranges from 0.001% to 10% by weight relative to the total weight of the composition.

15. The composition according to claim 14, wherein the amount of organic acid ranges from 0.05% to 2% by weight relative to the total weight of the composition.

16. The composition according to claim 1, further comprising a divalent mineral acid salt.

17. The composition according to claim 16, wherein the divalent mineral acid salt is chosen from ammonium sulfate, sodium hydrogen phosphate, sodium carbonate, and mixtures thereof.

18. The composition according to claim 16, wherein the amount of divalent mineral acid salt ranges from 0.001% to 10% by weight relative to the total weight of the composition.

19. The composition according to claim 18, wherein the amount of divalent mineral acid salt ranges from 0.05% to 2% by weight relative to the total weight of the composition.

20. The composition according to claim 1, further comprising at least one additional direct dye chosen from neutral, acidic or cationic nitrobenzene direct dyes, neutral, acidic or cationic azo direct dyes, neutral, acidic or cationic quinone direct dyes, azine direct dyes, triarylmethane direct dyes, indoamine direct dyes, and natural direct dyes.

21. The composition according to claim 1, further comprising at least one oxidation base chosen from para-phenylenediamines, bis(phenyl)alkylenediamines, para-aminophenols, ortho-aminophenols, heterocyclic bases, and addition salts thereof.

22. The composition according to claim 21, wherein the at least one oxidation base is present in an amount ranging from 0.001% to 10% by weight relative to the total weight of the composition.

23. The composition according to claim 1, further comprising at least one coupler chosen from meta-phenylenediamine couplers, meta-aminophenol couplers, meta-diphenol couplers, naphthalene-based couplers, heterocyclic couplers, and addition salts thereof.

24. The composition according to claim 23, wherein amount of the at least one coupler ranges from 0.001% to 10% by weight relative to the total weight of the composition.

25. The composition according to claim 1, further comprising at least one adjuvant chosen from anionic, cationic, nonionic, amphoteric and zwitterionic surfactants and mixtures thereof; anionic, cationic, nonionic, amphoteric and zwitterionic polymers and mixtures thereof; mineral and organic thickeners; antioxidants; penetrating agents; sequestering agents; fragrances; buffers; dispersants; conditioners; film-forming agents; ceramides; preserving agents, and opacifiers.

26. The composition according to claim 25, wherein each at least one adjuvant is present in an amount ranging from 0.01% to 20% by weight relative to the weight of the composition.

27. A process for the direct dyeing of keratin fibers, comprising
applying to the keratin fibers, for a time sufficient to obtain a desired coloration, a dye composition comprising:
at least one hydrophobic direct dye having a logP greater than 2, and
at least one organic or mineral acid with a pKa of less than 4.5,
in an aqueous-alcoholic dyeing medium comprising at least 60% water, wherein the pH of the composition is less than 7.

28. The direct dyeing process according to claim 27, wherein the application is performed at a temperature of less than or equal to 60° C.

29. The direct dyeing process according to claim 28, wherein the temperature ranges from 25° C. to 40° C.

30. The direct dyeing process according to claim 27, further comprising applying an oxidation composition comprising an oxidation agent to the keratin fibers simultaneously with or sequentially to the dye composition.

31. A process for increasing the color fastness of keratin fibers upon direct dyeing, said process comprising
applying to the keratin fibers for a time sufficient to obtain a desired coloration, a dye composition comprising:
at least one hydrophobic direct dye having a logP greater than 2, and
at least one organic or mineral acid with a pKa of less than 4.5,
in an aqueous-alcoholic dyeing medium comprising at least 60% water, wherein the pH of the composition is less than 7, and
wherein the at least one direct dye and the at least one acid are present in the aqueous-alcoholic medium in a combined amount sufficient to give increased color-fastness to the keratin fibers.

* * * * *